(12) United States Patent
Martin et al.

(10) Patent No.: US 8,267,689 B2
(45) Date of Patent: Sep. 18, 2012

(54) DESCRIBING A PERIODONTAL DISEASE STATE

(75) Inventors: John A. Martin, State College, PA (US); Roy C. Page, Mount Vernon, WA (US); Carl F. Loeb, Mount Vernon, WA (US)

(73) Assignee: PreViser Corporation, Mount Vernon, WA (US)

( * ) Notice: Subject to any disclaimer, the term of this patent is extended or adjusted under 35 U.S.C. 154(b) by 1888 days.

(21) Appl. No.: 11/281,241

(22) Filed: Nov. 17, 2005

(65) Prior Publication Data

US 2006/0154210 A1 Jul. 13, 2006

Related U.S. Application Data

(60) Provisional application No. 60/629,033, filed on Nov. 18, 2004.

(51) Int. Cl.
*A61C 5/00* (2006.01)
(52) U.S. Cl. ..................................... 433/215
(58) Field of Classification Search ............ 433/215
See application file for complete search history.

(56) References Cited

U.S. PATENT DOCUMENTS

| | | | | |
|---|---|---|---|---|
| 5,692,501 | A | 12/1997 | Minturn | 128/630 |
| 5,752,827 | A * | 5/1998 | Baron et al. | 433/68 |
| 5,755,571 | A * | 5/1998 | Companion | 433/72 |
| 2003/0053673 | A1* | 3/2003 | Dewaele | 382/132 |
| 2003/0202947 | A1* | 10/2003 | Szymaitis | 433/217.1 |

FOREIGN PATENT DOCUMENTS

| | | |
|---|---|---|
| EP | 1 293 925 | 3/2003 |
| JP | 08-173461 | 7/1996 |
| JP | 11-47095 | 2/1999 |
| JP | 2002-83044 | 3/2002 |
| WO | WO97/11635 | 4/1997 |

OTHER PUBLICATIONS

ADA Oral Health Topics. Retreived from http://www.ada.org/public/topics/periodontal_diseases.asp on Jun. 11, 2008 using the wayback machine internet archive for Oct. 29, 2004.*
Waybackmachine internet archive results for http://www.ada.org/public/topics/periodontal_diseases.asp.*
International Preliminary Report on Patentability for International Application No. PCT/US2005/041772 mailed May 31, 2007.
International Search Report for Application No. PCT/US2005/041772, dated Nov. 20, 2006.
Official Action mailed Sep. 14, 2007 from corresponding European Application 05851783.0.
Authorized officer Tetsunobu Miyagawa, Notification of Reasons for Refusal in Patent Application No. 2007-543261, mailed Jun. 7, 2011, 7 pages.
Authorized officer Ryan Reynolds, Canadian Intellectual Property Office, Office Action in Application No. 2,586,561, dated Sep. 26, 2011, 3 pages.

* cited by examiner

*Primary Examiner* — Heidi M Eide
(74) *Attorney, Agent, or Firm* — Fish & Richardson P.C.

(57) ABSTRACT

A method of describing a periodontal disease state includes assigning severity diagnoses to portions of a dentition, where the severity diagnoses correspond to periodontal disease states, and assigning numeric values to the portions, where the numeric values correspond to the severity diagnoses. The method also includes obtaining a raw score based on the numeric values, and determining a disease score based on the raw score. The disease score corresponds to a periodontal disease state of the dentition.

28 Claims, 20 Drawing Sheets

| Text-Linguistic Periodontal Diagnoses |
|---|
| Health |
| Gingivitis |
| Localized Mild Periodontitis<br>Generalized Mild Periodontitis |
| Localized Mild and Moderate Periodontitis<br>Localized Moderate Periodontitis<br>Generalized Mild to Moderate Periodontitis<br>Generalized Mild and Localized Moderate Periodontitis<br>Generalized Moderate Periodontitis |
| Localized Mild and Severe Periodontitis<br>Localized Moderate and Severe Periodontitis<br>Localized Severe Periodontitis<br>Generalized Mild to Severe Periodontitis<br>Generalized Mild and Localized Severe Periodontitis<br>Generalized Moderate to Severe Periodontitis<br>Generalized Moderate and Localized Severe Periodontitis<br>Generalized Severe Periodontitis |

FIG. 1
(Prior Art)

| Disease Score | Severity Category | Text-Linguistic Periodontal Diagnoses |
|---|---|---|
| 1 | Health | Health |
| 2-3 | Gingivitis | Gingivitis |
| 4-10 | Beginning Periodontitis | Localized Mild Periodontitis<br>Generalized Mild Periodontitis |
| 11-36 | Moderate Periodontitis | Localized Mild and Moderate Periodontitis<br>Localized Moderate Periodontitis<br>Generalized Mild to Moderate Periodontitis<br>Generalized Mild and Localized Moderate Periodontitis<br>Generalized Moderate Periodontitis |
| 37-100 | Severe Periodontitis | Localized Mild and Severe Periodontitis<br>Localized Moderate and Severe Periodontitis<br>Localized Severe Periodontitis<br>Generalized Mild to Severe Periodontitis<br>Generalized Mild and Localized Severe Periodontitis<br>Generalized Moderate to Severe Periodontitis<br>Generalized Moderate and Localized Severe Periodontitis<br>Generalized Severe Periodontitis |

FIG. 4

| Sextant Severity Diagnosis | Numeric Value per Sextant for Each Severity Diagnosis | | | | | |
|---|---|---|---|---|---|---|
| # of dentulous sextants that comprise the dentition → | 1 _192_ | 2 _194_ | 3 _196_ | 4 _198_ | 5 _200_ | 6 _202_ |
| Health | $2^0 = 1$ | $3^0 = 1$ | $4^0 = 1$ | $5^0 = 1$ | $6^0 = 1$ | $7^0 = 1$ |
| Gingivitis | $2^1 = 2$ | $3^1 = 3$ | $4^1 = 4$ | $5^1 = 5$ | $6^1 = 6$ | $7^1 = 7$ |
| Mild Periodontitis | $2^2 = 4$ | $3^2 = 9$ | $4^2 = 16$ | $5^2 = 25$ | $6^2 = 36$ | $7^2 = 49$ |
| Moderate Periodontitis | $2^3 = 8$ | $3^3 = 27$ | $4^3 = 64$ | $5^3 = 125$ | $6^3 = 216$ | $7^3 = 343$ |
| Severe Periodontitis | $2^4 = 16$ | $3^4 = 81$ | $4^4 = 256$ | $5^4 = 625$ | $6^4 = 1296$ | $7^4 = 2401$ |

The Sextant Numeric Value for an Edentulous Sextant is Always 0.

FIG. 7

| 210 → | 212 Upper Right | 214 Upper Anterior | 216 Upper Left | 218 Lower Left | 220 Lower Anterior | 222 Lower Right | 224 Raw Score | 226 Disease Score |
|---|---|---|---|---|---|---|---|---|
| 228 → | Mild Periodontitis =49 | Gingivitis =7 | Mild Periodontitis =49 | Gingivitis =7 | Gingivitis =7 | Gingivitis =7 | 126 | 7 |
| 230 → | Edentulous =0 | Gingivitis =6 | Mild Periodontitis =36 | Mild Periodontitis =36 | Gingivitis =6 | Gingivitis =6 | 90 | 7 |
| 232 → | Edentulous =0 | Gingivitis =5 | Edentulous =0 | Mild Periodontitis =25 | Gingivitis =5 | Gingivitis =5 | 40 | 7 |
| 234 → | Edentulous =0 | Edentulous =0 | Edentulous =0 | Mild Periodontitis =16 | Gingivitis =4 | Gingivitis =4 | 24 | 7 |
| 236 → | Edentulous =0 | Edentulous =0 | Edentulous =0 | Mild Periodontitis =9 | Edentulous =0 | Gingivitis =3 | 12 | 7 |

FIG. 8

| Disease Score | Text Description | 1 | 2 | 3 | 4 | 5 | 6 | 7 |
|---|---|---|---|---|---|---|---|---|
| | # of dentulous sextants in dentition ..> | | | | | | | |
| 0 | None | 0 | | | | | | |
| 1 | Health | | 1 | 2 | 3 | 4 | 5 | 6 |
| 2 | Gingivitis | | | | | | | 12 |
| 2 | Gingivitis | | | | 6 | 8 | 10 | 18 |
| 2 | Gingivitis | | | | 4 | | 12 | 15 | 24 |
| 3 | Gingivitis | | | | | 9 | | 20 | 30 |
| 3 | Gingivitis | | | | | | 16 | 25 | 36 |
| 3 | Gingivitis | | | 2 | 6 | 12 | 20 | 30 | 42 |
| 4 | Localized Mild Periodontitis | | | | | | | 54 |
| 4 | Localized Mild Periodontitis | | | | | | | 60 |
| 4 | Localized Mild Periodontitis | | | | | | | 66 |
| 5 | Localized Mild Periodontitis | | | | | | | 72 |
| 5 | Localized Mild Periodontitis | | | | | | | 78 |
| 5 | Localized Mild Periodontitis | | | | | | | 84 |
| 6 | Localized Mild Periodontitis | | | | | 18 | 28 | 40 | 102 |
| 6 | Localized Mild Periodontitis | | | | | | 32 | 45 | 108 |
| 6 | Localized Mild Periodontitis | | | | | 21 | 36 | 50 | 114 |
| 7 | Localized Mild Periodontitis | | | | | | | 55 | 120 |
| 7 | Localized Mild Periodontitis | | | | | 24 | 40 | 60 | 126 |
| 8 | Generalized Mild Periodontitis | | | 10 | | 52 | 75 | 150 |
| 8 | Generalized Mild Periodontitis | | | | | | 80 | 156 |
| 8 | Generalized Mild Periodontitis | | | | | 56 | 85 | 162 |
| 9 | Generalized Mild Periodontitis | | | 12 | | 60 | 90 | 168 |
| 9 | Generalized Mild Periodontitis | | | | 33 | | 110 | 198 |
| 9 | Generalized Mild Periodontitis | | | | | | 115 | 204 |
| 10 | Generalized Mild Periodontitis | | | | 36 | | 120 | 210 |
| 10 | Generalized Mild Periodontitis | | | | | | 76 | 145 | 246 |
| 10 | Generalized Mild Periodontitis | | | | | | 80 | 150 | 252 |
| 10 | Generalized Mild Periodontitis | | 4 | 18 | 48 | 100 | 180 | 294 |
| 11 | Localized Moderate Periodontitis | | | | | | | 348 |
| 11 | Localized Moderate Periodontitis | | | | | | | 354 |
| 11 | Localized Moderate Periodontitis | | | | | | | 360 |
| 12 | Localized Moderate Periodontitis | | | | | | | 366 |
| 12 | Localized Moderate Periodontitis | | | | | | | 372 |
| 12 | Localized Moderate Periodontitis | | | | | | | 378 |
| 13 | Localized Mild and Moderate Periodontitis | | | | | | | 396 |
| 13 | Localized Mild and Moderate Periodontitis | | | | | | | 402 |
| 13 | Localized Mild and Moderate Periodontitis | | | | | | | 408 |
| 14 | Localized Mild and Moderate Periodontitis | | | | | | | 414 |
| 14 | Localized Mild and Moderate Periodontitis | | | | | | | 420 |
| 15 | Generalized Mild to Moderate Periodontitis | | | | | | | 444 |
| 15 | Generalized Mild to Moderate Periodontitis | | | | | | | 450 |
| 15 | Generalized Mild to Moderate Periodontitis | | | | | | | 456 |
| 15 | Generalized Mild to Moderate Periodontitis | | | | | | | 462 |
| 16 | Generalized Mild and Localized Moderate Periodontitis | | | | | | | 492 |
| 16 | Generalized Mild and Localized Moderate Periodontitis | | | | | | | 498 |
| 17 | Generalized Mild and Localized Moderate Periodontitis | | | | | | | 504 |
| 18 | Generalized Mild and Localized Moderate Periodontitis | | | | | | | 540 |

FIG. 9A

| | | | | | | | |
|---|---|---|---|---|---|---|---|
| 18 | Generalized Mild and Localized Moderate Periodontitis | | | | | | 546 |
| 19 | Generalized Mild and Localized Moderate Periodontitis | | | | | | 588 |
| 20 | Localized Moderate Periodontitis | | | 66 | 128 | 220 | 690 |
| 20 | Localized Moderate Periodontitis | | | | | 225 | 696 |
| 20 | Localized Moderate Periodontitis | | | 69 | 132 | 230 | 702 |
| 21 | Localized Moderate Periodontitis | | | | 136 | 235 | 708 |
| 21 | Localized Moderate Periodontitis | | | 72 | 140 | 240 | 714 |
| 22 | Generalized Mild to Moderate Periodontitis | | | | | 255 | 738 |
| 22 | Generalized Mild to Moderate Periodontitis | | | | | 260 | 744 |
| 23 | Generalized Mild to Moderate Periodontitis | | | | | 265 | 750 |
| 23 | Generalized Mild to Moderate Periodontitis | | | | | 270 | 756 |
| 24 | Generalized Mild to Moderate Periodontitis | | | 81 | 152 | 290 | 786 |
| 24 | Generalized Mild to Moderate Periodontitis | | | | 156 | 295 | 792 |
| 25 | Generalized Mild to Moderate Periodontitis | | | 84 | 160 | 300 | 798 |
| 25 | Generalized Mild to Moderate Periodontitis | | | | 176 | 325 | 834 |
| 26 | Generalized Mild to Moderate Periodontitis | | | | 180 | 330 | 840 |
| 26 | Generalized Mild to Moderate Periodontitis | | | 96 | 200 | 360 | 882 |
| 27 | Generalized Moderate Periodontitis | | 28 | | 252 | 435 | 1032 |
| 27 | Generalized Moderate Periodontitis | | | | | 440 | 1038 |
| 28 | Generalized Moderate Periodontitis | | | | 256 | 445 | 1044 |
| 28 | Generalized Moderate Periodontitis | | 30 | | 260 | 450 | 1050 |
| 29 | Generalized Mild to Moderate Periodontitis | | | | | 470 | 1080 |
| 29 | Generalized Mild to Moderate Periodontitis | | | | | 475 | 1086 |
| 30 | Generalized Mild to Moderate Periodontitis | | | | | 480 | 1092 |
| 30 | Generalized Mild to Moderate Periodontitis | | | | 276 | 505 | 1128 |
| 31 | Generalized Mild to Moderate Periodontitis | | | | 280 | 510 | 1134 |
| 31 | Generalized Mild to Moderate Periodontitis | | 36 | | 300 | 540 | 1176 |
| 32 | Generalized Moderate Periodontitis | | | 129 | | 650 | 1374 |
| 32 | Generalized Moderate Periodontitis | | | | | 655 | 1380 |
| 33 | Generalized Moderate Periodontitis | | | 132 | | 660 | 1386 |
| 33 | Generalized Mild to Moderate Periodontitis | | | | | 685 | 1422 |
| 34 | Generalized Mild to Moderate Periodontitis | | | | | 690 | 1428 |
| 34 | Generalized Mild to Moderate Periodontitis | | | 144 | | 720 | 1470 |
| 35 | Generalized Moderate Periodontitis | | | | 376 | 865 | 1716 |
| 35 | Generalized Moderate Periodontitis | | | | 380 | 870 | 1722 |
| 36 | Generalized Mild to Moderate Periodontitis | | | | 400 | 900 | 1764 |
| 36 | Generalized Moderate Periodontitis | 8 | 54 | 192 | 500 | 1080 | 2058 |
| 37 | Localized Severe Periodontitis | | | | | | 2406 |
| 37 | Localized Severe Periodontitis | | | | | | 2412 |
| 38 | Localized Severe Periodontitis | | | | | | 2418 |
| 38 | Localized Severe Periodontitis | | | | | | 2424 |
| 39 | Localized Severe Periodontitis | | | | | | 2430 |
| 39 | Localized Severe Periodontitis | | | | | | 2436 |
| 40 | Localized Mild and Severe Periodontitis | | | | | | 2454 |
| 40 | Localized Mild and Severe Periodontitis | | | | | | 2460 |
| 41 | Localized Mild and Severe Periodontitis | | | | | | 2466 |
| 41 | Localized Mild and Severe Periodontitis | | | | | | 2472 |
| 42 | Localized Mild and Severe Periodontitis | | | | | | 2478 |
| 42 | Localized Mild and Severe Periodontitis | | | | | | 2502 |
| 43 | Localized Mild and Severe Periodontitis | | | | | | 2508 |
| 43 | Localized Mild and Severe Periodontitis | | | | | | 2514 |
| 43 | Localized Mild and Severe Periodontitis | | | | | | 2520 |
| 44 | Generalized Mild and Localized Severe Periodontitis | | | | | | 2550 |
| 44 | Generalized Mild and Localized Severe Periodontitis | | | | | | 2556 |
| 45 | Generalized Mild and Localized Severe Periodontitis | | | | | | 2562 |

FIG. 9B

| | | | | | | | |
|---|---|---|---|---|---|---|---|
| 45 | Generalized Mild and Localized Severe Periodontitis | | | | | | 2598 |
| 46 | Generalized Mild and Localized Severe Periodontitis | | | | | | 2604 |
| 46 | Generalized Mild and Localized Severe Periodontitis | | | | | | 2646 |
| 47 | Localized Moderate and Severe Periodontitis | | | | | | 2748 |
| 48 | Localized Moderate and Severe Periodontitis | | | | | | 2754 |
| 48 | Localized Moderate and Severe Periodontitis | | | | | | 2760 |
| 49 | Localized Moderate and Severe Periodontitis | | | | | | 2766 |
| 49 | Localized Moderate and Severe Periodontitis | | | | | | 2772 |
| 50 | Generalized Mild to Severe Periodontitis | | | | | | 2796 |
| 50 | Generalized Mild to Severe Periodontitis | | | | | | 2802 |
| 51 | Generalized Mild to Severe Periodontitis | | | | | | 2808 |
| 51 | Generalized Mild to Severe Periodontitis | | | | | | 2814 |
| 52 | Generalized Mild to Severe Periodontitis | | | | | | 2844 |
| 52 | Generalized Mild to Severe Periodontitis | | | | | | 2850 |
| 53 | Generalized Mild to Severe Periodontitis | | | | | | 2856 |
| 53 | Generalized Mild to Severe Periodontitis | | | | | | 2892 |
| 54 | Generalized Mild to Severe Periodontitis | | | | | | 2898 |
| 54 | Generalized Mild to Severe Periodontitis | | | | | | 2940 |
| 55 | Generalized Moderate to Severe Periodontitis | | | | | | 3090 |
| 55 | Generalized Moderate to Severe Periodontitis | | | | | | 3096 |
| 56 | Generalized Moderate to Severe Periodontitis | | | | | | 3102 |
| 56 | Generalized Moderate to Severe Periodontitis | | | | | | 3108 |
| 57 | Generalized Mild to Severe Periodontitis | | | | | | 3138 |
| 57 | Generalized Mild to Severe Periodontitis | | | | | | 3144 |
| 58 | Generalized Mild to Severe Periodontitis | | | | | | 3150 |
| 58 | Generalized Mild to Severe Periodontitis | | | | | | 3186 |
| 59 | Generalized Mild to Severe Periodontitis | | | | | | 3192 |
| 59 | Generalized Mild to Severe Periodontitis | | | | | | 3234 |
| 60 | Generalized Moderate to Severe Periodontitis | | | | | | 3432 |
| 60 | Generalized Moderate to Severe Periodontitis | | | | | | 3438 |
| 60 | Generalized Moderate to Severe Periodontitis | | | | | | 3444 |
| 61 | Generalized Mild to Severe Periodontitis | | | | | | 3480 |
| 62 | Generalized Mild to Severe Periodontitis | | | | | | 3486 |
| 62 | Generalized Mild to Severe Periodontitis | | | | | | 3528 |
| 63 | Generalized Moderate and Localized Severe Periodontitis | | | | | | 3774 |
| 63 | Generalized Moderate and Localized Severe Periodontitis | | | | | | 3780 |
| 64 | Generalized Moderate and Localized Severe Periodontitis | | | | | | 3822 |
| 64 | Generalized Moderate and Localized Severe Periodontitis | | | | | | 4116 |
| 65 | Localized Severe Periodontitis | | | 258 | 628 | 1300 | 4806 |
| 65 | Localized Severe Periodontitis | | | | | 1305 | 4812 |
| 66 | Localized Severe Periodontitis | | | 261 | 632 | 1310 | 4818 |
| 67 | Localized Severe Periodontitis | | | | 636 | 1315 | 4824 |
| 67 | Localized Severe Periodontitis | | | 264 | 640 | 1320 | 4830 |
| 68 | Generalized Mild to Severe Periodontitis | | | | | 1335 | 4854 |
| 68 | Generalized Mild to Severe Periodontitis | | | | | 1340 | 4860 |
| 69 | Generalized Mild to Severe Periodontitis | | | | | 1345 | 4866 |
| 69 | Generalized Mild to Severe Periodontitis | | | | | 1350 | 4872 |
| 70 | Generalized Mild to Severe Periodontitis | | | 273 | 652 | 1370 | 4902 |
| 70 | Generalized Mild to Severe Periodontitis | | | | 656 | 1375 | 4908 |
| 71 | Generalized Mild to Severe Periodontitis | | | 276 | 660 | 1380 | 4914 |
| 71 | Generalized Mild to Severe Periodontitis | | | | 676 | 1405 | 4950 |
| 72 | Generalized Mild to Severe Periodontitis | | | | 680 | 1410 | 4956 |
| 72 | Generalized Mild to Severe Periodontitis | | | 288 | 700 | 1440 | 4998 |
| 73 | Generalized Moderate to Severe Periodontitis | | | | | 1515 | 5148 |
| 73 | Generalized Moderate to Severe Periodontitis | | | | | 1520 | 5154 |

FIG. 9C

| # | Diagnosis | | | | | | |
|---|---|---|---|---|---|---|---|
| 74 | Generalized Moderate to Severe Periodontitis | | | | | 1525 | 5160 |
| 74 | Generalized Moderate to Severe Periodontitis | | | | | 1530 | 5166 |
| 75 | Generalized Mild to Severe Periodontitis | | | | | 1550 | 5196 |
| 75 | Generalized Mild to Severe Periodontitis | | | | | 1555 | 5202 |
| 76 | Generalized Mild to Severe Periodontitis | | | | | 1560 | 5208 |
| 76 | Generalized Mild to Severe Periodontitis | | | | | 1585 | 5244 |
| 77 | Generalized Mild to Severe Periodontitis | | | | | 1590 | 5250 |
| 77 | Generalized Mild to Severe Periodontitis | | | | | 1620 | 5292 |
| 78 | Generalized Moderate to Severe Periodontitis | | | | 321 | 752 | 1730 | 5490 |
| 78 | Generalized Moderate to Severe Periodontitis | | | | | 756 | 1735 | 5496 |
| 79 | Generalized Moderate to Severe Periodontitis | | | | 324 | 760 | 1740 | 5502 |
| 79 | Generalized Mild to Severe Periodontitis | | | | | 776 | 1765 | 5538 |
| 80 | Generalized Mild to Severe Periodontitis | | | | | 780 | 1770 | 5544 |
| 80 | Generalized Mild to Severe Periodontitis | | | | 336 | 800 | 1800 | 5586 |
| 81 | Generalized Moderate to Severe Periodontitis | | | | | 876 | 1945 | 5832 |
| 81 | Generalized Moderate to Severe Periodontitis | | | | | 880 | 1950 | 5838 |
| 82 | Generalized Mild to Severe Periodontitis | | | | | 900 | 1980 | 5880 |
| 82 | Generalized Moderate to Severe Periodontitis | | | | 384 | 1000 | 2160 | 6174 |
| 83 | Generalized Severe Periodontitis | | | 82 | | 1252 | 2595 | 7206 |
| 83 | Generalized Severe Periodontitis | | | | | 2600 | 7212 |
| 84 | Generalized Severe Periodontitis | | | | 1256 | 2605 | 7218 |
| 84 | Generalized Severe Periodontitis | | | 84 | | 1260 | 2610 | 7224 |
| 85 | Generalized Mild to Severe Periodontitis | | | | | 2630 | 7254 |
| 85 | Generalized Mild to Severe Periodontitis | | | | | 2635 | 7260 |
| 86 | Generalized Mild to Severe Periodontitis | | | | | 2640 | 7266 |
| 86 | Generalized Mild to Severe Periodontitis | | | | 1276 | 2665 | 7302 |
| 87 | Generalized Mild to Severe Periodontitis | | | | 1280 | 2670 | 7308 |
| 87 | Generalized Mild to Severe Periodontitis | | | 90 | | 1300 | 2700 | 7350 |
| 88 | Generalized Moderate to Severe Periodontitis | | | | | 2810 | 7548 |
| 88 | Generalized Moderate to Severe Periodontitis | | | | | 2815 | 7554 |
| 88 | Generalized Moderate to Severe Periodontitis | | | | | 2820 | 7560 |
| 89 | Generalized Mild to Severe Periodontitis | | | | | 2845 | 7596 |
| 89 | Generalized Mild to Severe Periodontitis | | | | | 2850 | 7602 |
| 90 | Generalized Mild to Severe Periodontitis | | | | | 2880 | 7644 |
| 91 | Generalized Moderate to Severe Periodontitis | | | | 1376 | 3025 | 7890 |
| 91 | Generalized Moderate to Severe Periodontitis | | | | 1380 | 3030 | 7896 |
| 92 | Generalized Mild to Severe Periodontitis | | | | 1400 | 3060 | 7938 |
| 92 | Generalized Moderate to Severe Periodontitis | | | 108 | | 1500 | 3240 | 8232 |
| 93 | Generalized Severe Periodontitis | | | | 513 | 1876 | 3890 | 9606 |
| 93 | Generalized Severe Periodontitis | | | | | 3895 | 9612 |
| 94 | Generalized Severe Periodontitis | | | | 516 | 1880 | 3900 | 9618 |
| 94 | Generalized Mild to Severe Periodontitis | | | | | 3925 | 9654 |
| 95 | Generalized Mild to Severe Periodontitis | | | | | 3930 | 9660 |
| 95 | Generalized Mild to Severe Periodontitis | | | | 528 | 1900 | 3960 | 9702 |
| 96 | Generalized Moderate to Severe Periodontitis | | | | | 4105 | 9948 |
| 96 | Generalized Severe Periodontitis | | | | | 4110 | 9954 |
| 97 | Generalized Mild to Severe Periodontitis | | | | | 4140 | 9996 |
| 97 | Generalized Moderate to Severe Periodontitis | | | | 576 | 2000 | 4320 | 10290 |
| 98 | Generalized Severe Periodontitis | | | | | 5185 | 12006 |
| 98 | Generalized Severe Periodontitis | | | | | 5190 | 12012 |
| 99 | Generalized Mild to Severe Periodontitis | | | | | 5220 | 12054 |
| 99 | Generalized Moderate to Severe Periodontitis | | | | | 5400 | 12348 |
| 100 | Generalized Severe Periodontitis | | 16 | 162 | 768 | 2500 | 6480 | 14406 |

FIG. 9D

| Diagnosis | Sextant | | |
|---|---|---|---|
| | Upper Right | Upper Anterior | Upper Left |
| Edentulous | | - | |
| Health | | - | |
| Gingivitis | | - | |
| Slight/Mild/Beginning Periodontitis | | - | |
| Moderate Periodontitis | | - | |
| Severe Periodontitis | | - | |
| | | | |
| Diagnosis | Sextant | | |
| | Lower Right | Lower Anterior | Lower Left |
| Edentulous | - | | - |
| Health | - | | - |
| Gingivitis | - | | - |
| Slight/Mild/Beginning Periodontitis | - | | - |
| Moderate Periodontitis | - | | - |
| Severe Periodontitis | - | | - |
| | | | |
| Disease Score | 52 | Raw Score | |
| Text-linguistic Diagnosis | Generalized Mild Severe Periodontitis | | |

FIG. 11

| Diagnosis | Sextant | | |
|---|---|---|---|
| | Upper Right | Upper Anterior | Upper Left |
| Bone Height <2mm | | – | |
| Bone Height 2-4mm | | – | |
| Bone Height >4mm | | – | |
| Pocket Depth <5mm | | – | |
| Pocket Depth 5-7mm | | – | |
| Pocket Depth >7mm | | – | |
| | | | |
| Diagnosis | Sextant | | |
| | Lower Right | Lower Anterior | Lower Left |
| Bone Height <2mm | – | | – |
| Bone Height 2-4mm | – | | – |
| Bone Height >4mm | – | | – |
| Pocket Depth <5mm | – | | – |
| Pocket Depth 5-7mm | – | | – |
| Pocket Depth >7mm | – | | – |
| | | Yes | No |
| Bleeding | | | |
| Disease Score | 44 | Raw Score | 2550 |
| Text-linguistic Diagnosis | Generalized Mild and Localized Severe Periodontitis | | |

| When Patient has not Already Been Referred | |
|---|---|
| Referral to a periodontist is strongly recommended | |
| Referral to a periodontist should be considered | |
| Referral to a periodontist might be considered | |
| Insufficient current basis for referral to a periodontist | |

| | Score Range | | | | | |
|---|---|---|---|---|---|---|
| Current Disease Score | >=93 | Severe Periodontitis | | 302 | | |
| | 83-92 | Severe Periodontitis | | | | |
| | 65-82 | Severe Periodontitis | | | | |
| | 37-64 | Severe Periodontitis | | | | |
| | 27-36 | Moderate Periodontitis | | 304 | | |
| | 11-26 | Moderate Periodontitis | | | | |
| | 8-10 | Mild Periodontitis | | 306 | | |
| | 4-7 | Mild Periodontitis | | | | |
| | 1-3 | Health Gingivitis | | 308 | | |

| When Patient has not Already Been Referred | |
|---|---|
| Referral to a periodontist is strongly recommended | |
| Referral to a periodontist should be considered | |
| Referral to a periodontist might be considered | |
| Insufficient current basis for referral to a periodontist | |

| | | | | | | | |
|---|---|---|---|---|---|---|---|
| | | | | | | | |
| | | | | | | | |
| Current Risk Score | 5 | | }336 | | | | |
| | 4 | | | | | | |
| | 3 | | }334 | | | | |
| | 2 | | }332 | | | | |
| | 1 | | | | | | |

FIG. 15

| When Patient has not Already Been Referred | | | | | | | | |
|---|---|---|---|---|---|---|---|---|
| Referral to a periodontist is strongly recommended | | | | | | | | |
| Referral to a periodontist should be considered | | | | | | | | |
| Referral to a periodontist might be considered | | | | | | | | |
| Insufficient current basis for referral to a periodontist | | | | | | | | |
| | | | | | | | | |
| | | Current Disease Score 352 | | | | | | |
| Score Range | 1-3 | 4-7 | 8-10 | 11-26 | 27-36 | 37-64 | 65-82 | 83-92 | >=93 |
| Severity Category | Health-Gingivitis | Mild Periodontitis | Mild Periodontitis | Moderate Periodontitis | Moderate Periodontitis | Severe Periodontitis | Severe Periodontitis | Severe Periodontitis | Severe Periodontitis |
| Current Risk Score — 5 | | | | | | | | | |
| 4 | | | | | | | | | |
| 3 | | | | | | | | | |
| 2 | | | | | | | | | |
| 1 | | | | | | | | | |

FIG. 17

DESCRIBING A PERIODONTAL DISEASE STATE

CROSS-REFERENCE TO RELATED APPLICATIONS

This application claims priority under 35 U.S.C. §119 to U.S. Provisional Patent Application Ser. No. 60/629,033, filed Nov. 18, 2004, and entitled "DESCRIBING A PERIODONTAL DISEASE STATE", the entire contents of which are hereby incorporated by reference.

TECHNICAL FIELD

This patent application relates generally to a method of describing a periodontal disease state and, more particularly, to a method that describes the periodontal disease state numerically.

BACKGROUND

While several diseases can affect the periodontium, plaque associated periodontal diseases are by far the most commonly observed. These infectious diseases have been classified as gingivitis, chronic periodontitis, aggressive periodontitis, periodontitis associated with systemic disease, necrotizing periodontitis, periodontal abscess, and periodontic-endodontic lesions. Gingivitis and chronic and aggressive periodontitis comprise, by far, the most commonly observed periodontal conditions.

Periodontal diseases are classified, and a diagnosis is made, based on a comprehensive periodontal examination. Factors upon which these decisions are made include dental and medical histories, assessment of gingival inflammation (e.g., bleeding on probing), probing pocket depth, extent and pattern of alveolar bone loss, and presence or absence of signs and symptoms including pain, ulceration, and amount of observable plaque and calculus.

FIG. 1 shows a table 10 of common terminology used to provide a diagnosis for periodontal disease. The diagnosis designates the disease state extent as generalized or localized and severity as mild, moderate, or severe. Using this terminology, seventeen text-linguistic diagnoses are possible. Use of traditional text-linguistic terminology for a diagnosis of periodontitis based primarily on periodontal pocket depth, the extent and pattern of alveolar bone loss and bleeding on probing can be insufficiently precise to support clinical decision making or involvement of patients in successful management of their periodontal disease.

The traditional periodontal diagnoses (e.g., the text-linguistic diagnoses in FIG. 1) lack descriptive precision to accurately describe a periodontal disease state. For example, a diagnosis of generalized severe periodontitis can include a wide range of individuals extending from those who manifest only a few pockets that measure 6 mm or deeper in all sextants with mild to moderate bone loss to individuals with terminal disease. An individual with a specific diagnosis can undergo considerable improvement or deterioration in status without an accompanying change in diagnosis. The lack of a clear, concise, accurate nomenclature that is sensitive to small changes adversely affects a patient's understanding of their condition and poorly defines the urgency of their situation. Similarly dentists cannot know with precision the effectiveness of treatment when there is a broad range of meaning as occurs with text nomenclature.

SUMMARY

Described herein is a method to quantify periodontal disease states using a numeric scale of 1 to 100. The method is based on a combination of sextant diagnoses determined by pocket depth, alveolar bone loss and bleeding on probing using mathematic theory and periodontal principles. The numeric score is, generally speaking, more readily understandable and more useful than the traditional text nomenclature. Furthermore, the use of a numeric periodontal disease score provides a clinician with a more precise assessment and expression of periodontal status and changes in status over time. In addition, use of the score may improve patient involvement in their care and treatment decisions formulated by their dentist, resulting in better health care outcomes.

In some embodiments, a method of describing a periodontal disease state includes assigning severity diagnoses to portions of a dentition, the severity diagnoses corresponding to periodontal disease states and assigning numeric values to the portions, the numeric values corresponding to the severity diagnoses. The method also includes obtaining a raw score based on the numeric values and determining a disease score based on the raw score. The disease score corresponds to a periodontal disease state of the dentition.

Embodiments can include one or more of the following.

Obtaining the raw score can include summing the numeric values. Determining the disease score can include correlating the raw score to the disease score. The portions can include sextants of the dentition. The severity diagnoses can include one or more of healthy, gingivitis, mild periodontitis, moderate periodontitis, and severe periodontitis. The severity diagnoses can be determined based on bleeding that occurs upon probing in the portion, tooth pocket depth in the portion, and radiographic bone distance from a cemento-enamel junction in the portion.

The method can also include measuring the bleeding that occurs upon probing based on one point in the dentition, measuring tooth pocket depth based on six points in the dentition, and measuring radiographic bone distance from a cemento-enamel junction based on six points in the portion. The method can also include using the disease score to determine a premium for an insurance policy. The method can also include monitoring a change in the disease score over time and adjusting the premium in accordance with the change. The disease score can include a numeric value in a range of 1 to 100.

In some embodiments, a machine-readable medium can store executable instructions for use in describing a periodontal disease state. The instructions can be capable of causing a machine to receive severity diagnoses for portions of a dentition, the severity diagnoses corresponding to periodontal disease states, assign numeric values to the portions, the numeric values corresponding to the severity diagnoses, obtain a raw score based on the numeric values, and determine a disease score based on the raw score, the disease score corresponding to a periodontal disease state of the dentition.

Embodiments can include one or more of the following.

The instructions for obtaining the raw score can include instructions for summing the numeric values. The instructions for determining the disease score can include instructions for correlating the raw score to the disease score. The portions can include sextants of the dentition. The severity diagnoses can include one or more of healthy, gingivitis, mild periodontitis, moderate periodontitis, and severe periodontitis. The severity diagnoses can be determined based on bleeding that occurs upon probing in the portion, tooth pocket depth in the portion, and radiographic bone distance from a cemento-enamel junction in the portion.

The machine-readable medium can also include instructions to use the disease score to determine a premium for an insurance policy. The machine-readable medium can also include instructions to monitor a change in the disease score over time and adjust the premium in accordance with the change. The disease score can be a numeric value in a range of 1 to 100.

Other features and advantages described herein will be apparent from the description, the drawings, and the claims.

DESCRIPTION OF THE DRAWINGS

FIG. 1 is a table containing text-linguistic diagnoses of periodontal disease.

FIG. 4 is a table containing text-linguistic diagnoses of periodontal disease and the corresponding numeric disease score grouped by severity categories.

FIG. 7 is a table showing assignment of numeric values to sextants based on each sextant's severity diagnosis.

FIG. 8 is a table showing correlation of raw scores to diagnosis scores.

FIGS. 9A-9D is a table showing the possible combinations of dentulous sextants and their corresponding raw scores, disease scores, and text description.

FIG. 11 is a user interface used in determining disease scores based on diagnosis.

FIG. 12 is a user interface used in determining disease scores based on pocket depth, bone height and bleeding.

FIG. 13 is a chart of a referral recommendation based on current disease score.

FIG. 15 is a chart of a referral recommendation based on current risk score.

FIG. 17 is a chart of a referral recommendation based on current disease score and current risk score.

Like reference numerals in different figures indicate like elements.

DETAILED DESCRIPTION

Figure 2:
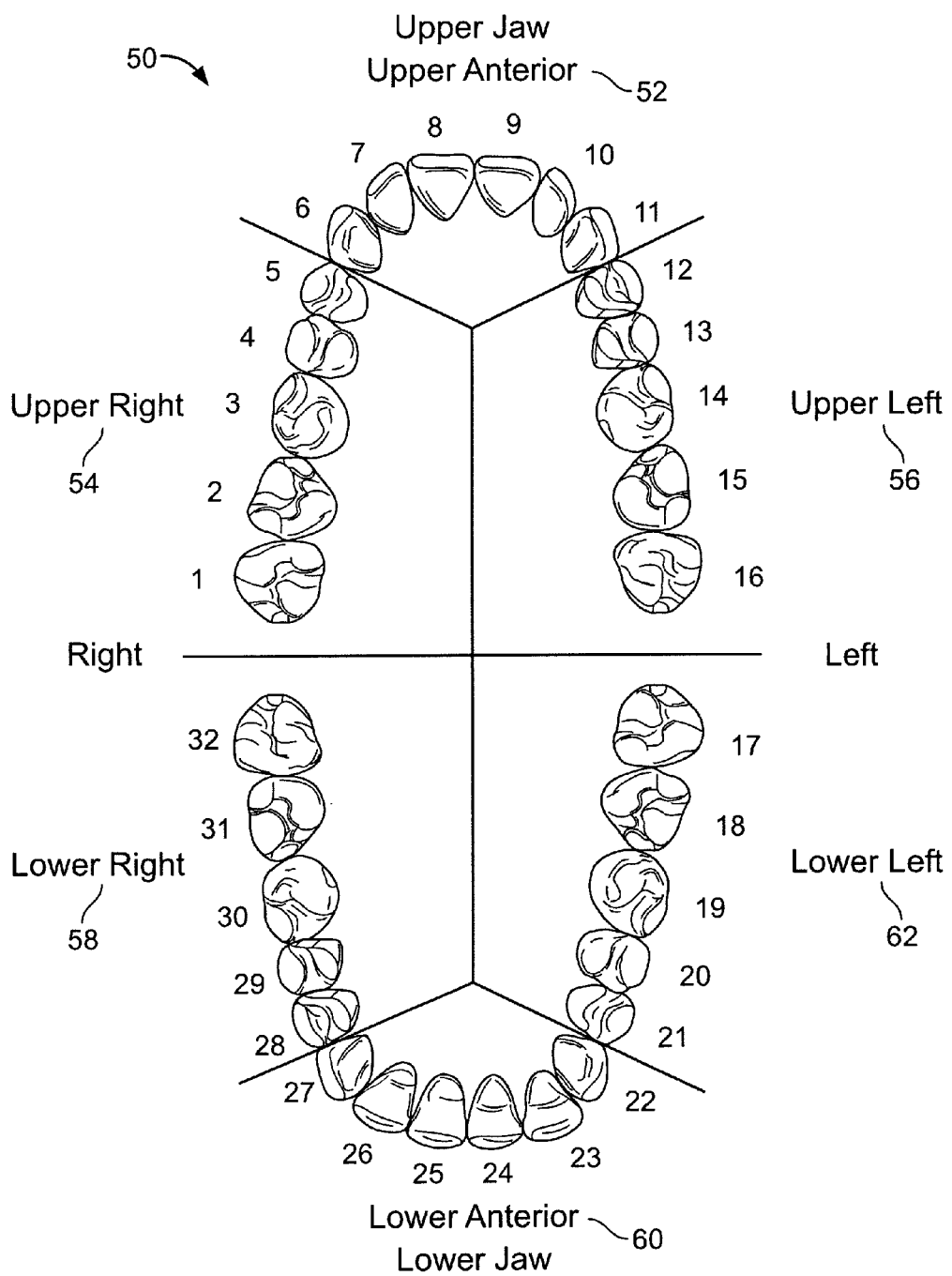
FIG. 2 is a diagram of a dentition.

Referring to FIG. 2, a dentition or set of teeth 50 is shown. A full dentition includes 32 teeth, sixteen of which are included in the upper jaw and sixteen of which are included in the lower jaw. Four teeth are third molars (wisdom teeth), which are generally absent resulting in the typical dentition having 28 teeth. In general, a diagnosis represents a snapshot of the health of the teeth in the dentition at a specific moment. The diagnosis may be measured by signs and symptoms that are traditionally described using text-linguistic nomenclature (e.g., as shown in FIG. 1).

Figure 3:
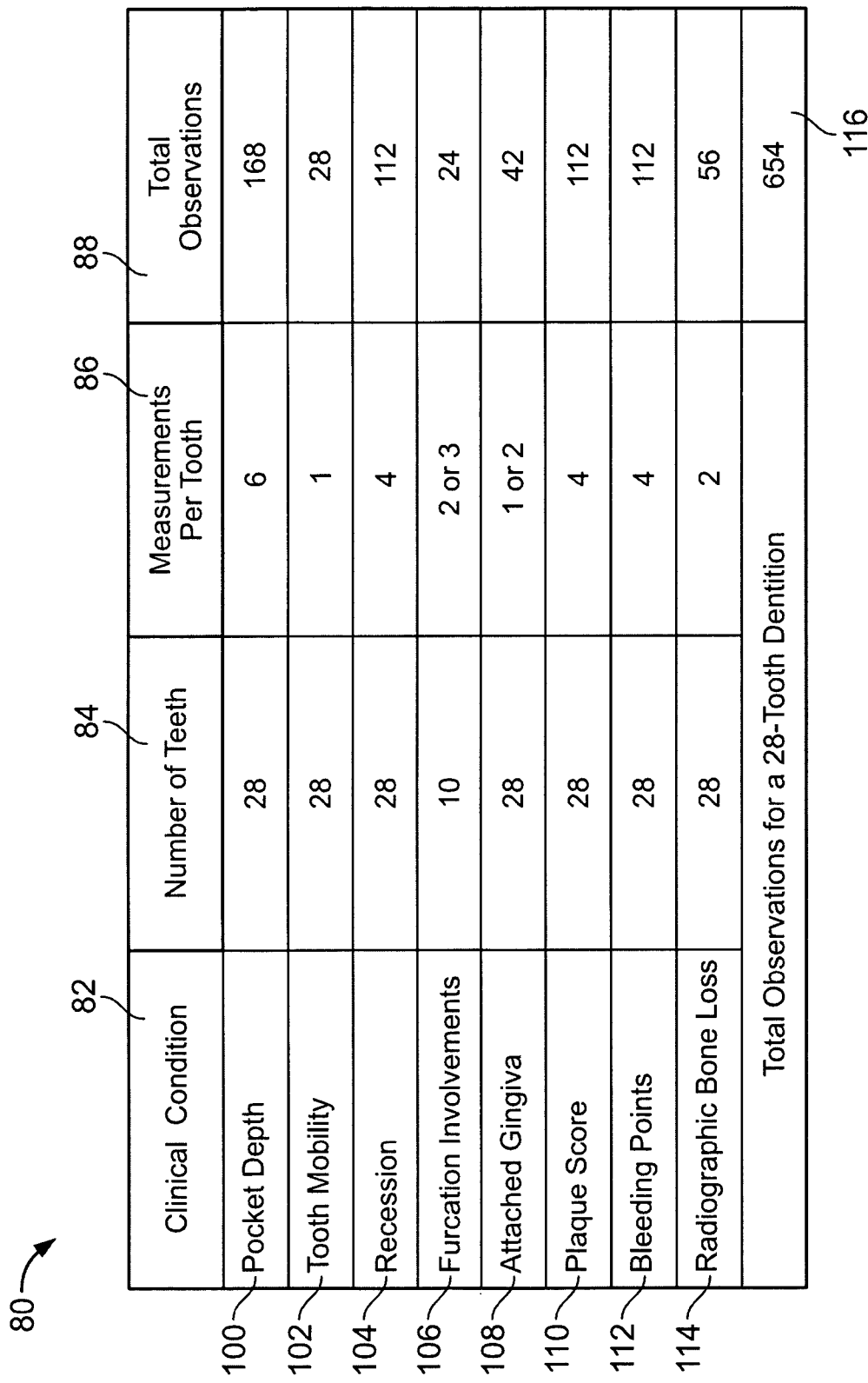
FIG. 3 is a table indicating a number of measurements and observations used to, establish a diagnosis of periodontal disease.

As shown in FIG. 3, an exemplary periodontal diagnosis for an entire dentition is a composite summary of 22 to 25 observations 80 for each tooth. These observations include some or all of a pocket depth 100, tooth mobility 102, recession 104, furcation involvements 106, attached gingiva 108, a plaque score 110, bleeding points 112, and radiographic bone loss 114. The number of teeth for which these observations is taken is shown in column 84 and the number of measurements per tooth for each condition is shown in column 86. By summing the total number of observations 116, a periodontal diagnosis for a 28-tooth dentition includes approximately 654 observations.

A periodontal diagnosis requires the correlation of individual tooth diagnoses. The groupings of individual tooth diagnoses constitute the realm of permutations and combinations. A permutation is the term used to describe possible groupings where the order is important. Permutations of diagnoses for teeth is the number of different severity diagnosis for each tooth listed in the sequence of tooth #1, 2, 3, . . . 32. Regardless of the ease or complexity of determining the severity of disease for a single tooth, there is a need for a method to aggregate and correlate the full spectrum of possible combinations of disease severity for a 28-tooth dentition. This need is not surprising since a 28-tooth dentition has $5^{28}$ or $3.7 \times 10^{19}$ permutations and 35,960 combinations of possible disease states using 5 severity types (health, gingivitis, and mild, moderate, and severe periodontitis) for each tooth. Combinations, which differ from permutations by eliminating the requirement of order (e.g., number of teeth with severe, moderate, and mild periodontitis, gingivitis, and health) reduces the number to 35,960 combinations. This number is still too large for a practical application.

To facilitate practical clinical usability, the method described herein (referred to henceforth as "the numeric method") uses the sextant of a dentition as the unit of measure to calculate a periodontal disease state that accurately describes disease severity and extent. Sextants, have $5^6$ or 15,625 permutations and 210 combinations. The former includes too many variations for practical use but the latter is usable. For the patient with 5, 4, 3, 2, or 1 dentulous sextants the number of possible sextant disease severity combinations would be 126, 70, 35, 15, and 5, respectively.

Thus, the sextant of a dentition is used as the unit of measure because the sextant is the smallest unit that is practical for routine clinical dentistry based on the number of permutations and combinations.

Referring back to FIG. 2, a full dentition 50 can be divided into six sextants 52, 54, 56, 58, 60, and 62. These sextants 52, 54, 56, 58, 60, and 62 group the teeth as belonging to either the upper jaw or lower jaw and group the teeth in the upper jaw and lower jaw into three sections each. These sections are referred to as upper right 54, upper anterior 52, upper left 56, lower right 58, lower anterior 60, and lower left 62. Each sextant includes five or six teeth. The sextant of a dentition is used as the unit of measure because the sextant is the smallest unit that is practical for routine clinical dentistry based on the number of permutations and combinations. However, other subdivisions, such as quadrants may be used. Additionally the use of subdivisions allows periodontal treatment to be planned and implemented by sextants or quadrants instead of on a tooth-by-tooth basis.

As shown in FIG. 4, a disease score 132 can be generated based on the numeric method described herein for determining the health of the dentition. The disease score 132 has a range from one, which indicates a healthy periodontium, to one hundred for the most severe disease condition. In comparison to the text-linguistic periodontal diagnoses shown in FIG. 1, this one to one hundred numeric scale expands the number of possible diagnoses by nearly six-fold. In addition, to aid in communication, general severity category indicators 134 can be associated with particular ranges of disease scores 132. In general, the use of a numeric disease score provides various advantages such as allowing the progression of disease to be more accurately tracked over time.

Figure 5:
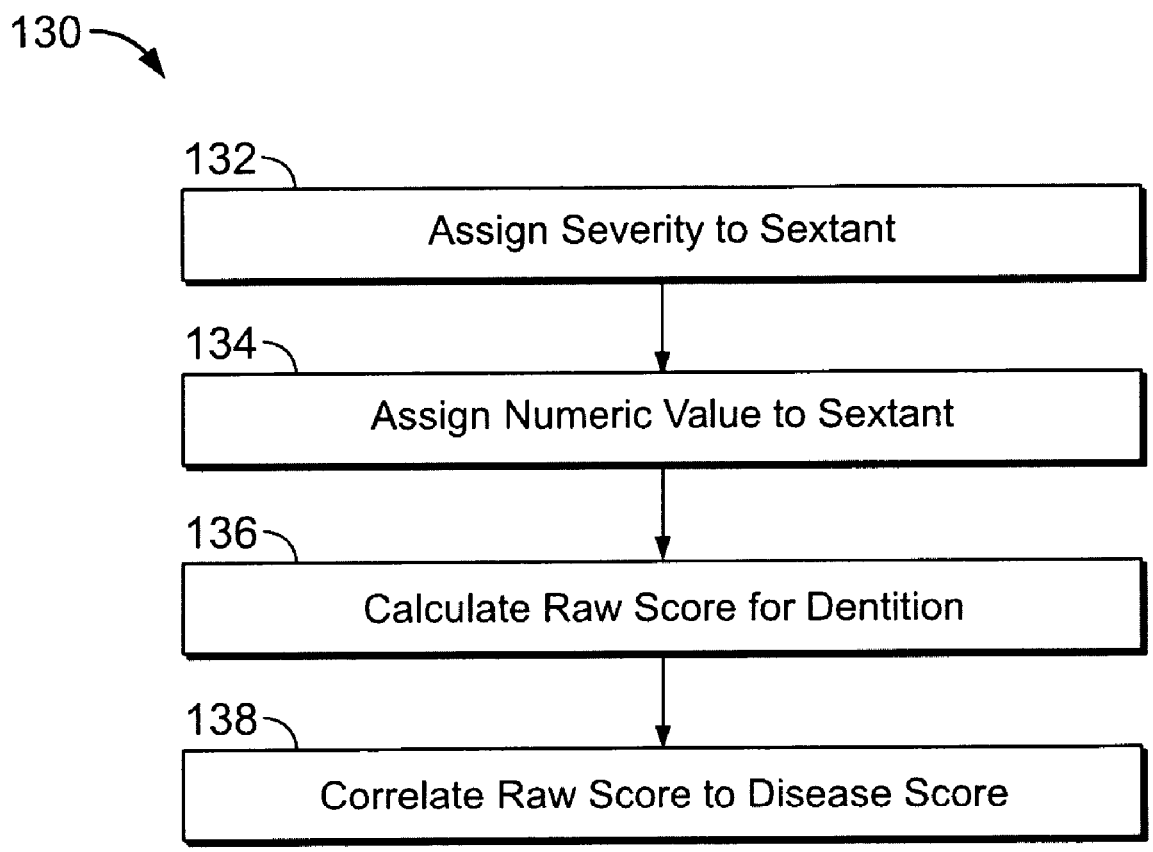
FIG. 5 is a flow chart of a process for determining a periodontal disease score.

Referring to FIG. 5, a process 130 is shown for determining a numeric periodontal disease state score based on a numeric method. Process 130 may be performed, at least in part, with the aid of computer hardware and software. For example, the computer may receive inputs related to observations performed by a dentist and then perform additional calculations or actions automatically (e.g., without further dentist input). Process 130 includes assigning 132 a severity diagnosis to each sextant based on observations of the periodontal tissues, assigning 134 a numeric value to the observations for the sextant, calculating 136 a raw score for the dentition based on the numeric values for the sextants, and correlating 138 the raw score to a disease state score, each of which is discussed below.

Figure 6A:
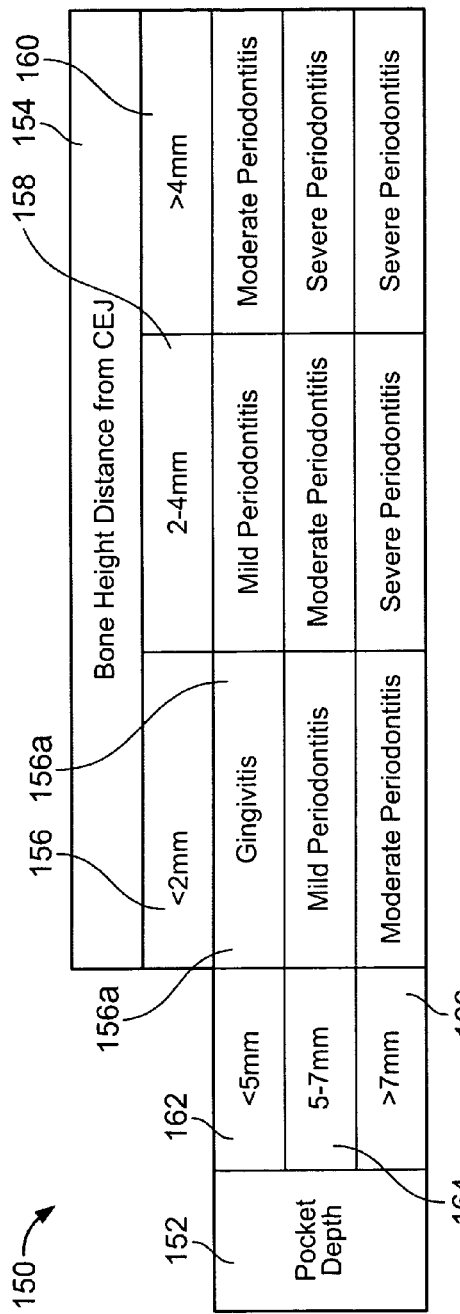
FIGS. 6A and 6B are tables showing severity diagnoses assigned to sextants based on pocket depth and radiographic bone height distance from the cemento-enamel junction.
Figure 6B:
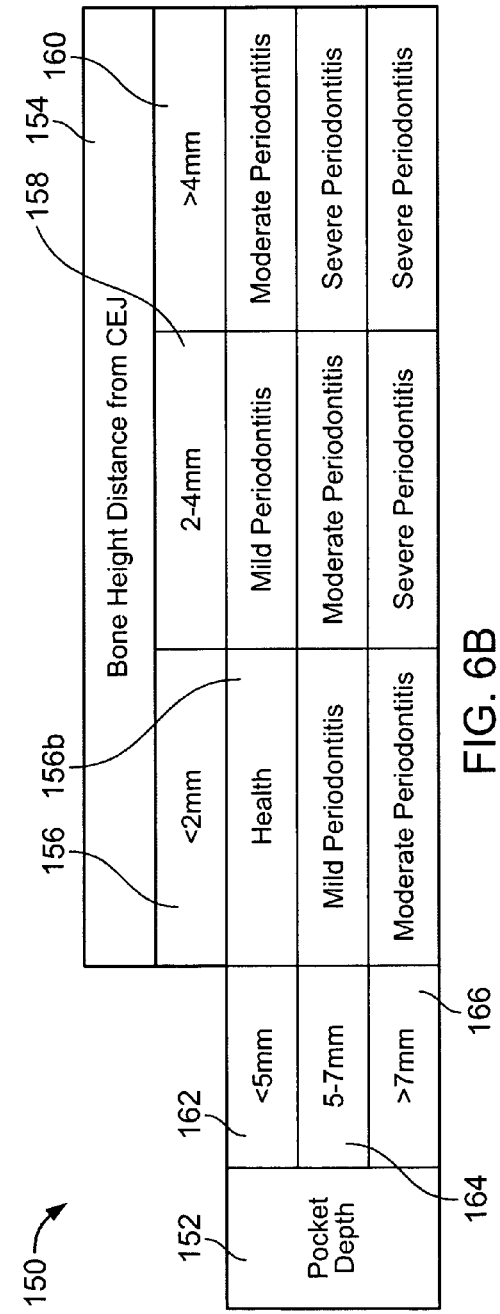

As described above, one step in calculating the disease score is assigning 132 a severity diagnosis to each sextant based on observations of the periodontal tissues in the sextant. Observations of the periodontal tissues include bleeding on probing, deepest pocket, and greatest radiographic bone height distance from the cemento-enamel junction (CEJ). Referring to FIGS. 6A and 6B, a combination of these observations can be used to determine the health of a particular sextant by providing a matrix of disease states for a sextant based on the greatest pocket depth 152 and the bone height distance from cemento-enamel junction 154. Bleeding on probing can also be considered in determining the health of the sextant. Bleeding on probing affects the diagnosis only when pocket depth is less than 5 mm and bone height is less than 2 mm (e.g., as shown in blocks 156a and 156b of FIGS. 6A and 6B respectively), where the existence of bleeding on probing signifies a diagnosis of gingivitis for the sextant and the absence of bleeding on probing signifies a diagnosis of health for the sextant.

As shown in FIGS. 6A and 6B, a three-point scale is used to measure pocket depth, which includes less than 5 mm (row 162), 5-7 mm (row 164), and greater than 7 mm (row 166). A 3-point scale is also used to measure radiographic bone height, and includes less than 2 mm (column 156), 2-4 mm (column 158), and greater than 4 mm (column 160) measurement observations. It is believed that the use of a 3-point scale for the pocket depth measurement 152 and bone height measurement 154 facilitates reasonable clinical accuracy without necessitating special calibration training of dental professionals.

The dental professional uses the combination of an observed bone height distance 154 and pocket depth 152 to determine the disease state for the sextant. For example, if the dental professional measures a bone height distance of 3 mm and a pocket depth of 8 mm, based on chart 150, the disease state for the sextant would be severe periodontitis.

Referring back to FIG. 5, subsequent to assigning 132 a severity to each sextant, the periodontal disease state determination process 130 includes determining 134 a numeric value for each sextant based on the sextant's severity diagnosis and the number of dentulous sextants that comprise the dentition (e.g., the number of sextants that have teeth). The numeric value will differ depending on the number of dentulous sextants included in the dentition. In assigning the numeric value to the various sextants, edentulous (i.e., toothless) sextants are assigned a value of zero. A logarithmic scale is utilized to determine these numeric values to ensure that once reduced to a 1 to 100 scale as described below, each point on the 1 to 100 scale describes a unique state of disease. Subsequent to assigning 132 a severity to each sextant, process 130 calculates a raw score 136. The raw score may be calculated by summing the numeric values for each of the dentulous sextants.

Referring to FIG. 7, a table 180 for calculating the raw score for a dentition is shown. Table 180 includes numeric values for each sextant severity diagnosis based on the number of dentulous sextants in the dentition. In table 180, the columns (e.g., columns 192, 194, 196, 198, 200 and 202) correspond to the number of dentulous sextants and the rows correspond to the sextant severity diagnosis for a sextant. After determining the severity diagnosis for a particular sextant, the table 180 can be used to determine a numeric value associated with the sextant. For example, if a dentition had one dentulous sextant, the values listed in column 192 would be used, if the dentition two dentulous sextants, the values listed in column 194 would be used, if the dentition three dentulous sextants, the values listed in column 196 would be used, if the dentition four dentulous sextants, the values listed in column 198 would be used, if the dentition five dentulous sextants, the values listed in column 200 would be used and, if the dentition six dentulous sextants, the values listed in column 202 would be used. For each sextant, a numeric value for the disease state is provided in rows 182, 184, 186, 188, and 190. A summation of the scores for each sextant provides the raw score.

Referring to FIG. 8, examples of the calculation of the raw score (shown in column 224) are shown. In a first example, row 228 shows the calculation of a raw score 224 for a dentition having six dentulous sextants. Since there are six sextants with teeth, based on the table shown in FIG. 7, column 202 is used to determine the numeric value for each sextant. In this example, the upper right sextant (column 212 of FIG. 8) and the upper left sextant (column 216 of FIG. 8) have a disease state of mild periodontitis. Therefore, using table 180, the numeric value for these sextants is the intersection of column 202 and row 186, i.e., 49. In this example, the remaining four sextants have a disease state of gingivitis. Therefore, the numeric value is the intersection of column 202 and row 184 in FIG. 7, i.e., 7. The raw score for the dentition is the summation of the numeric values for each of the sextants or 49+7+49+7+7+7 or 126.

In another example, row 230 shows the calculation of a raw score 224 for a dentition having five dentulous sextants. Table 180 shown in FIG. 7, in particular column 200, is used to determine the numeric value for each sextant. In this example, the upper left sextant (column 216) and the lower left sextant (column 218) have a disease state of mild periodontitis. Therefore, the numeric value for these sextants is the intersection of column 200 and row 186 in FIG. 7, i.e., 36. In this example, the remaining three sextants have a disease state of gingivitis. Therefore, the numeric value is the intersection of column 200 and row 184, i.e., 6. The edentulous sextant is assigned a value of zero. The raw score is the summation of the numeric values for each of the sextants or 0+6+36+36+6+6 which sums to 90.

Rows 232, 234, and 236 provide examples of the calculation of raw scores for dentitions having four, three, and two dentulous sextants respectively.

Figure 10:
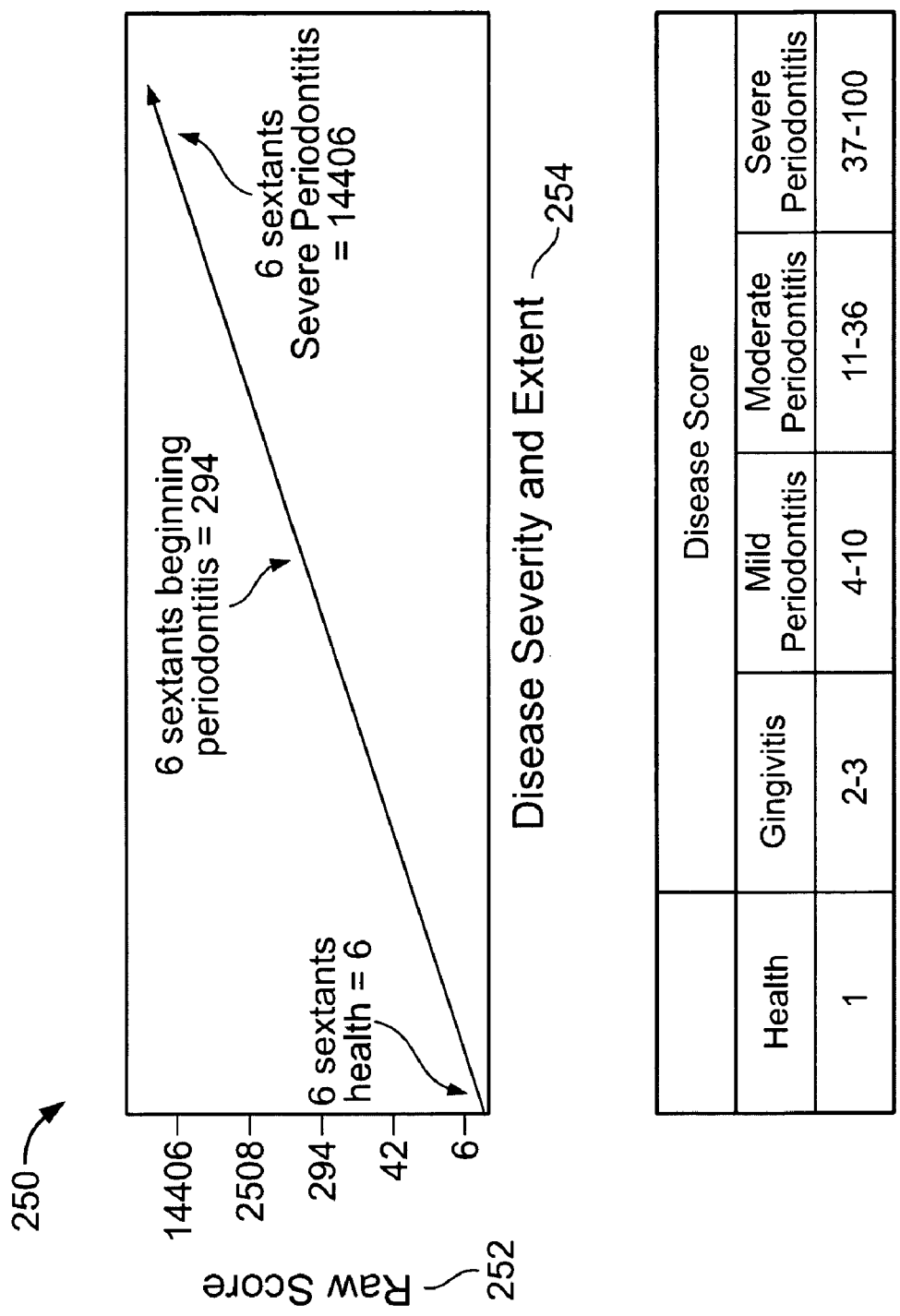
FIG. 10 is a graph showing the correlation of raw and disease scores.

Referring back to FIG. 5 the raw score is calculated and correlated 138 to a disease score ranging from one to one hundred. Referring to FIGS. 9A-9D, each combination of sextant disease severity represented numerically by the raw score is correlated using, e.g., the table of FIG. 9A-9D, to a disease score and an accompanying text description (other disease scores and associated raw scores are possible). The correlation can be based on a mapping of all of the possible raw scores for a dentition having a particular number of dentulous sextants to a one to one hundred scale. As shown in FIG. 10, the correlation of the raw score to the disease score can also be represented graphically. FIG. 10 shows a graph 250 where the raw score is on the Y-axis 252 of the graph and the disease score 254 is on the X-axis of the graph for a dentition having six dentulous sextants.

For example, referring back to the example shown in row 228 of FIG. 8, a patient with a full complement of teeth (six dentulous sextants) with the upper right and upper left sextants having mild periodontitis and the remaining 4 sextants having gingivitis has a raw score of 126. The raw score of 126 (shown in column 266f) is correlated to a disease score of 7 (shown in column 262) with a text description of localized mild periodontitis (shown in column 264)(see 270).

The numeric method is sufficiently robust to accommodate every number of dentulous sextants that a patient can present. In addition to the fully dentulous condition, Table 210 shown in FIG. 8, includes 4 partially edentulous conditions representing patients with 5, 4, 3, and 2 dentulous sextants with comparable combinations of sextant disease severity. The numeric method assigns the same disease score and text diagnosis for these situations, maintaining consistency of a diagnosis for comparable conditions.

The numeric method is a simple yet powerful way to describe a patient's current periodontal disease state. The information contained in a 100-point numeric scale is more descriptive than current text usage by a factor of six. By virtue of being numeric, changes in a patient's health state can be expressed, visually graphed, and understood readily. With the numeric method, an average of two or fewer combinations of sextant severity diagnoses correspond to one disease score making reasonably small changes detectable. This information can serve to guide future treatment decisions, as ineffective treatment would be identified by a higher disease score and effective treatment by a lower disease score. Such information would be valuable for an individual patient or a population of patients.

A patient who lacks understandable information about their current disease state cannot participate effectively in his or her own disease prevention and health improvement. It is believed that by quantifying the individual's periodontal condition in an objective and repeatable manner can provide various advantages. For example, the numeric method can create an environment in which the results of therapeutic interventions can be identified in terms of their success in improving health. The numeric method can also provide feedback to a patient that encourages and supports the patient's involvement in their own health care and the effect their own activities can have on their quality of life.

It is also believed that the numeric method is advantageous due to the limited data needed to determine the disease score. Only thirteen data points are used to calculate the disease score: six (one per sextant) for pocket depth, six (one per sextant) for bone height, and one for bleeding on probing. This is a small subset of the observations routinely documented in a clinical setting, thereby simplifying the utilization of the numeric method. The disease score is not intended to be a substitute for a comprehensive periodontal examination including the traditional periodontal charting, but is intended to supplement it by summarizing this information to increase its utility.

Additionally periodontal treatment is planned and implemented and insurance benefits determined by sextants or quadrants, not teeth. A 100-point scale is used because it is an established and easily understood means of measurement, although other scales may be used. Furthermore, correlating combinations to this scale is workable when the sextant is used as the unit of measure. Six sextants require compressing the 210 combinations by a factor of 2.1 to 1 for the 100-point scale. Five sextants require a compression of 1.26 to 1 and only some of the 100 disease scores are utilized when the number of sextants is less than five.

The numeric method satisfies the requirement that each raw score uniquely identify a distinct severity-extent combination. While large, the raw sextant numeric values shown in FIG. 9A-9D are sufficiently low to satisfy this requirement and avoid differing sextant disease combinations sharing the same raw score and disease score. The correlation of these raw scores to a 1 to 100 scale creates a measurement system of significant utility that facilitates understanding for both patient and clinician.

An exemplary uniform scoring system for five severity-extent categories would be 1-20 for health, 21-40 for gingivitis, 41-60 for mild periodontitis, 61-80 for moderate periodontitis, and 81-100 for severe periodontitis. The non-uniformity of score distribution in the numeric method occurs as a condition of the combination process in which the sextant with the most advanced disease severity is used for categorization. This creates 64 combinations where one or more sextants have severe periodontitis, 26 combinations where no sextant has severe periodontitis and one or more has moderate periodontitis, seven combinations where no sextant has severe or moderate periodontitis and one or more has mild periodontitis, and so forth concluding with two combinations for the gingivitis category and only one for health.

The numeric method establishes consistency of disease scores regardless of the number of teeth or dentulous sextants. This means that two patients, one with only lower teeth and the other with 28 teeth, could share a disease score of 7 that would accurately describe a similar condition. The former would have one sextant with mild periodontitis and two with gingivitis whereas the latter would have two sextants with mild periodontitis and four with gingivitis. In each case, one third of the dentulous sextants have mild periodontitis and two-thirds gingivitis.

The assignment of a severity diagnosis described in FIGS. 6A and 6B is but one way of designating a diagnosis. Disease is generally acknowledged when pocket depth is 5 mm or greater or bone height is 2 mm or more from the cemento-enamel junction. No other guidelines that assign a severity diagnosis exist. Nevertheless, the numeric method retains its validity with any set of rules or definitions that assign a severity diagnosis to a sextant.

As shown in FIGS. 11 and 12, the numeric method may employ a computer for routine clinical use. FIG. 11 shows an exemplary user interface 280 for entering data regarding the health of a dentition as well as calculating the raw score, disease score, and providing the text diagnosis is shown. In order to generate a diagnosis using user interface 280, a technician or user enters the disease state for each of the six sextants of the dentition using the selection blocks 282. If a sextant does not have any teeth, the block for edentulous would be selected for that sextant. Based on this user interface, only 6 data points may be entered by the user to determine the disease score. The computer uses the entries to automatically calculate the raw score (shown in block 286) and correlate the raw score to a disease score (shown in block 284) and a textual diagnosis (shown in block 288).

FIG. 12 shows another exemplary user interface for entering data regarding the health of a dentition as well as calculating the raw score, disease score, and providing the text diagnosis. In this example, the user enters two values for each sextant, a pocket depth and a bone height. As a stand-alone application, only thirteen data points need to be entered (e.g., two for each of the six sextants and one to indicate whether bleeding is present), taking only a few minutes of additional time, which would be a reasonable change in normal office procedures and workflow considering the multitude of significant benefits the disease score provides. Existing dental practice management systems and other computer-based dental applications can be easily adapted to incorporate the numeric method.

The disease score, or a change therein, can be of considerable value to a dentist and patient in determining whether and when to initiate periodontal care and specific treatment recommendations. High scores would indicate a need for more treatment, whereas low scores would indicate a need for less treatment. An increase in the disease score may indicate that more or different treatment is needed. A decrease in the disease score may indicate that the selected treatment was effective. Changes in the disease scores over time reveal effectiveness of treatment and provide a powerful method to continually and dynamically select the best treatment. Referral guidelines can be established using the current disease score and historical increases.

As shown in FIG. 13, the disease score can be used to determine whether or not to refer a patient to a periodontist. FIG. 13 shows a chart 300 for determining a referral status based on the current disease score (e.g., as listed in column 310). Disease scores from 1-3 (e.g., as indicated by grouping 308) are related to disease conditions that do not need to be referred to a periodontist. Disease scores from 4-10 (e.g., as indicated by grouping 306) are related to disease conditions in which referral to a periodontist might be considered. Disease scores from 11-36 (e.g., as indicated by grouping 304) are related to disease conditions in which referral to a periodontist should be considered and disease scores from 37-100 (e.g., as indicated by grouping 302) are related to disease conditions in which referral to a periodontist is strongly recommended. Various other groupings are possible.

Figure 14:
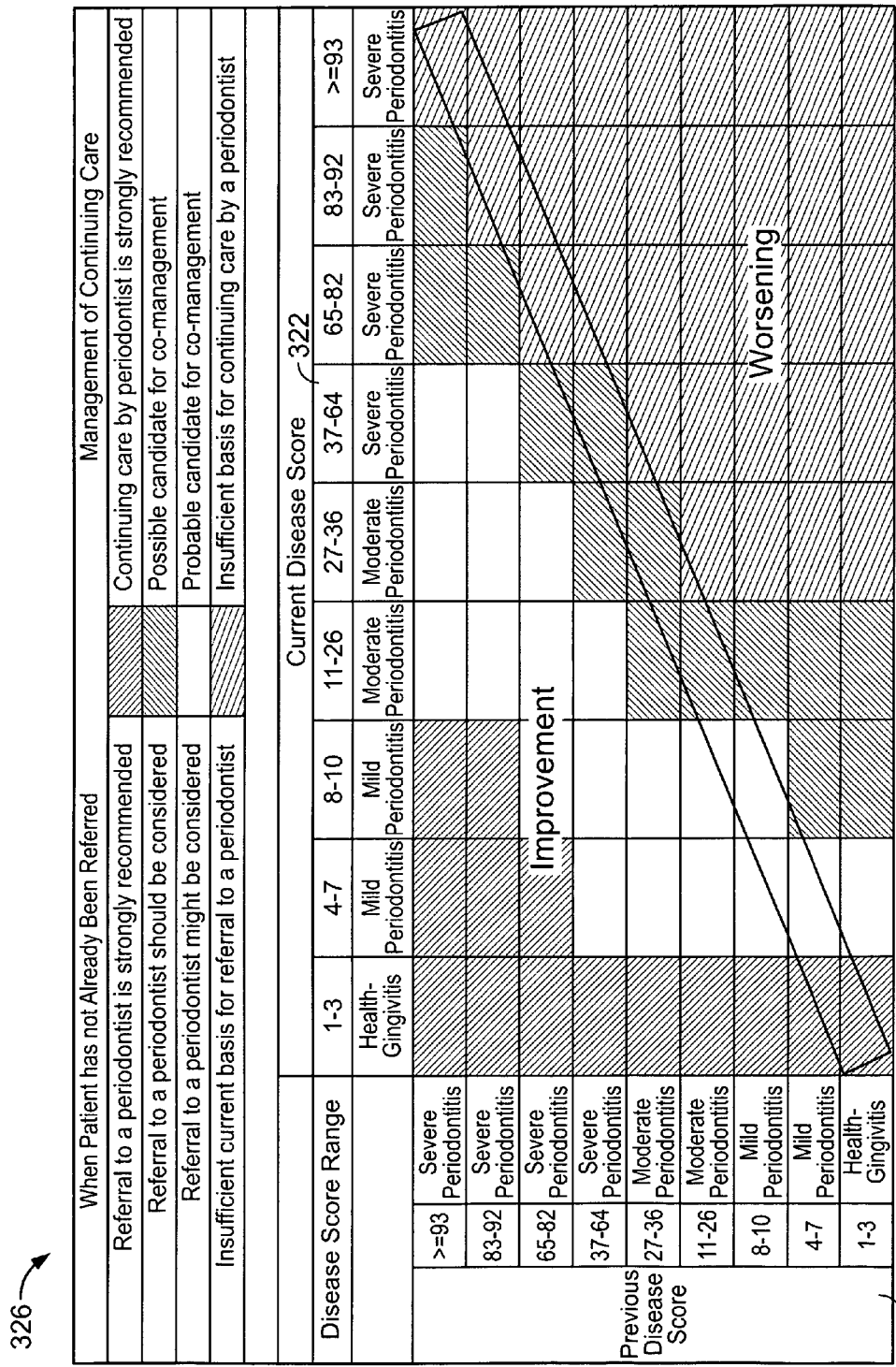
FIG. 14 is a chart of a referral recommendation based on current disease score and previous disease score.

As shown in FIG. 14, in some cases it can be beneficial to determine a recommendation based on both the current disease score (shown in columns 322) and a previous disease score (shown in rows 324). By using both the current disease score and the previous disease score, the determination of whether to refer a patient to a periodontist takes into account both the current state of the disease as well as whether the condition is improving or worsening. For example, referral will be less likely for a particular disease state if the condition has improved since the previous measurement and will be more likely if the disease score has increased (i.e., the condition has worsened).

In some embodiments, a risk score can be used to further enhance periodontal diagnosis, treatment planning and communicating this information to the patient. The use of a disease score and risk score may improve patient involvement in their care and treatment decisions formulated by their dentist resulting in better health care outcomes. A risk score, and method for determining the risk score, is described in U.S. Pat. No. 6,484,144, the contents of which are incorporated by reference into the subject application as if set forth herein in full. In general, the risk score is a predictive measure of the likelihood that the severity and extent of the disease will worsen.

As shown in FIG. 15, the risk score can be used by itself to determine if a referral to a periodontist should be made. As shown in chart 330, if a patient has a risk score of one or two (e.g., as indicated by grouping 332) the patient does not need to be referred to a periodontist. If a patient has a risk score of three (e.g., as indicated by grouping 334) referral to a periodontist should be considered. If a patient has a risk score of four or five (e.g., as indicated by grouping 336) referral to a periodontist is strongly recommended.

Figure 16:
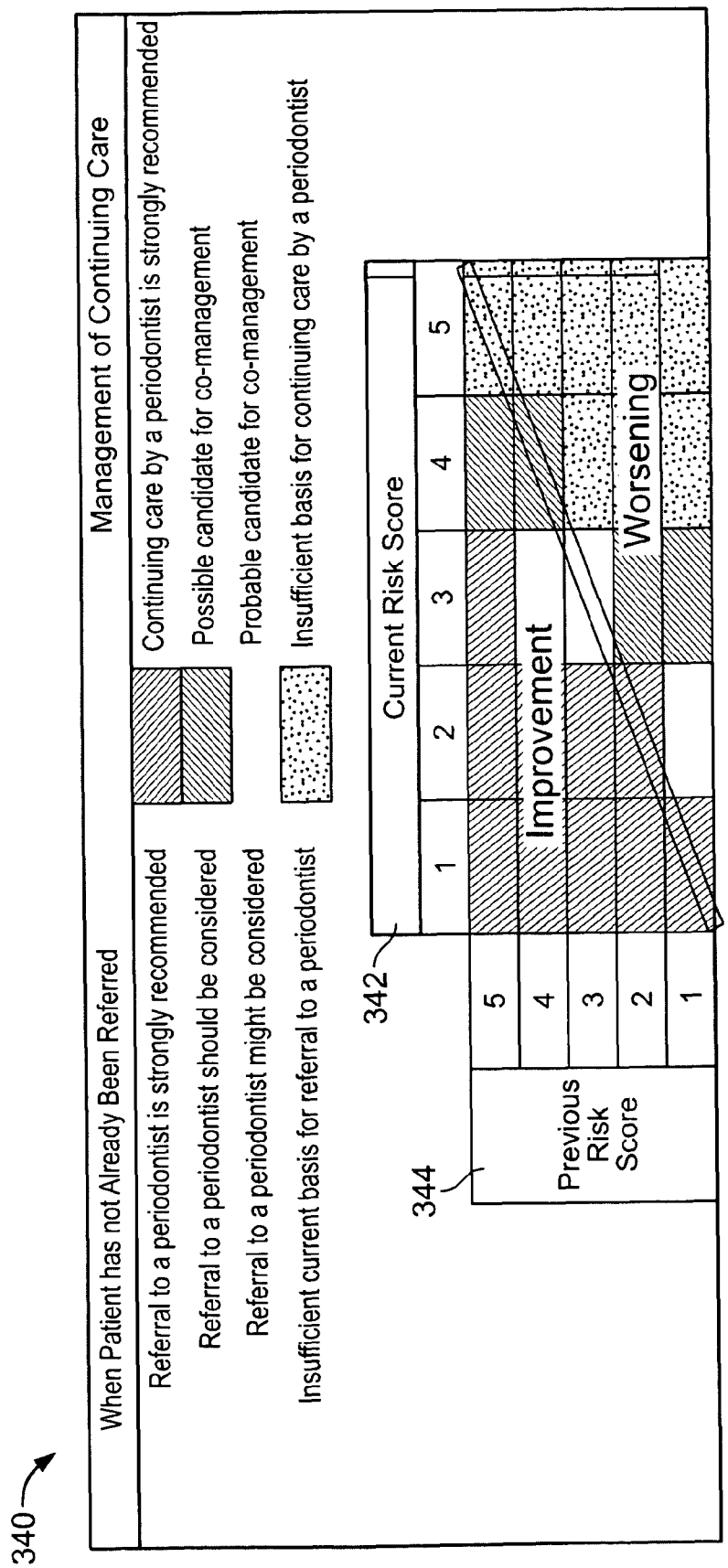
FIG. 16 is a chart of a referral recommendation based on current risk score and previous risk score.

As shown in FIG. 16, in some cases it can be beneficial to determine a recommendation based on both the current risk score (shown in columns 342) and a previous risk score (shown in rows 344). By using both the current risk score and the previous risk score, the determination of whether to refer a patient to a periodontist takes into account both the current risk condition as well as whether the condition is improving or worsening. For example, referral will be less likely for a particular risk score if the risk score has decreased and will be more likely if the risk score has increased (i.e., the condition has worsened).

As shown in FIG. 17, in some embodiments, the disease score can be coupled with a value that predicts a future disease state (e.g., the risk score), to further enhance periodontal diagnosis, treatment planning and communicating this information to the patient. Chart 350 provides a relationship between a disease score 352 and a current risk score 354 used to determine a referral status. Using chart 350, a dentist can make an informed decision regarding whether to refer the patient to a periodontist. For example, if the patient has moderate periodontitis with a disease score in the range of 27-36, referral will be strongly recommended if the patient has a risk score of four or five, referral should be considered if the patient has a risk score of 3, and referral might be considered if the patient has a risk score of one or two.

In general, the disease score simplifies and standardizes clinical documentation that summarizes a patient's periodontal disease state. The disease score could be used to justify treatment to third party payers, such as insurance companies, which would relieve dental staff from duplicating and submitting periodontal charting and radiographs, and which would relieve insurance personnel from managing disparate dental records.

In this regard, current health insurance policy underwriting procedures are frequently based on actuarial population data. Individuals of the same gender within broad age groups, and absent previously identified health problems, will receive essentially the same premium cost. The assignment of a mathematically derived individual health score to members of an insured group will allow far greater precision in differentiating the probable cost of care for individuals within the group. As a consequence, the use of the numeric method allows more efficient pricing of premiums for health care, with greater benefits available to individuals with greater disease scores, while still providing lower but still appropriate benefit levels for individuals with lower disease scores.

The numeric method also makes possible a quantification of changes in disease states for a population. For example, an average disease score of 28 on a 100 point scale represents a definable average level of disease within a group. If this score moves towards health as a result of care provided under the health insurance policy, the degree of improvement can be quantified, group premiums can be adjusted, and the improved health state accurately communicated to employer-payers of the insurance policy.

The numeric method is not limited in terms of use with computer hardware and/or software; it may find applicability in any computing or processing environment and with any type of machine that is capable of running machine-readable instructions. The numeric method can be implemented in conjunction with digital electronic circuitry, or in computer hardware, firmware, software, or in combinations thereof.

The numeric method can be implemented, at least in part, via a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps associated with the numeric method can be performed by one or more programmable processors executing one or more computer programs to perform the functions of the numeric method. The method steps can also be performed by, and the numeric method can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer include a processor for executing instructions and one or more memory devices for storing instructions and data. Generally, a computer will also include, or be operatively coupled to receive data from, or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks.

The numeric method can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the numeric method, or any combination of such back-end, middleware, or front-end components. The components of the system can be interconnected by any form or medium of digital data communication, e.g., a communication network. Examples of communication networks include a LAN and a WAN, e.g., the Internet.

Method steps associated with the numeric method can be rearranged and/or one or more such steps can be omitted to achieve the same, or similar, results to those described herein. The numeric method may be fully automated, meaning that it operate without user intervention, or interactive, meaning that all or part of the numeric method may include some user intervention.

Elements of different embodiments described herein may be combined to form other embodiments not specifically set forth above. Other embodiments not specifically described herein are also within the scope of the following claims.

What is claimed is:

1. A computer-implemented method of describing a periodontal disease state, comprising:
    receiving multiple inputs for each of a plurality of portions of a dentition, the inputs being based on observations of periodontal tissues for each portion of the dentition;
    assigning a severity diagnoses to the portions of the dentition, the severity diagnoses corresponding to periodontal disease states and being based on the received inputs based on the observations of the periodontal tissues and a predetermined correlation between a combination of observations of the periodontal tissues and a severity diagnosis;
    assigning, using a computer system configured to calculate a raw score and determine a disease score using a look up table, numeric values to the portions of the dentition, the numeric values corresponding to the severity diagnoses for each of the portions of the dentition, wherein the numeric values corresponding to the severity diagnoses differ based on the number of dentulous portions of the dentition;
    calculating, using the computer system configured to calculate the raw score and determine the disease score using a look up table, the raw score based on the numeric values assigned to the portions of the dentition; and
    using the look up table to determine the disease score based on the raw score, the disease score corresponding to a periodontal disease state of the dentition and being based on the periodontal disease states of multiple different portions of the dentition, wherein the disease score describes both the severity and the extent of periodontal disease in the dentition.

2. The method of claim 1, wherein calculating the raw score comprises summing the numeric values.

3. The method of claim 1, wherein determining the disease score comprises correlating the raw score to the disease score.

4. The method of claim 1, wherein the portions comprise sextants of the dentition and the disease score is based on the number of sextants of the dentition that include teeth.

5. The method of claim 1, wherein the severity diagnoses comprise one or more of healthy, gingivitis, mild periodontitis, moderate periodontitis, and severe periodontitis.

6. The method of claim 5, wherein the severity diagnoses are assigned based on bleeding that occurs upon probing in the portion, tooth pocket depth in the portion, and radiographic bone distance from a cemento-enamel junction in the portion.

7. The method of claim 6, further comprising:
    measuring the bleeding that occurs upon probing based on one point in each portion;
    measuring tooth pocket depth based on one point in each portion; and
    measuring radiographic bone distance from a cemento-enamel junction based on one point in each portion.

8. The method of claim 1, further comprising:
    using the disease score to determine a premium for an insurance policy.

9. The method of claim 8, further comprising:
    monitoring a change in the disease score over time; and
    adjusting the premium in accordance with the change.

10. The method of claim 1, wherein the disease score comprises a numeric value in a range of 1 to 100.

11. The method of claim 1, wherein assigning the numeric values to the portions of the dentition further comprises assigning the numeric values to the portions of the dentition using a method that assigns a numeric value for each severity diagnosis where the sum of the numeric values for all of the portions is unique for each combination of portions that is comprised of a unique number of severity diagnosis.

12. The method of claim 1, wherein the look-up table correlates every possible raw score with a specific disease score.

13. The method of claim 1, wherein the disease extent described by the disease score describes the percentage of portions with each severity diagnosis.

14. The method of claim 1, further comprising:
monitoring a change in the disease score over time, wherein the disease score increases and decreases based on therapeutic response.

15. The method of claim 1, wherein the computer system configured to calculate the raw score and determine the disease score using the look up table comprises the computer system programmed to calculate the raw score and determine the disease score.

16. A machine-readable medium that stores executable instructions for use in describing a periodontal disease state, the instructions causing a machine to:
receive data to assign severity diagnoses for portions of a dentition, the severity diagnoses corresponding to periodontal disease states, the data including multiple inputs for each of a plurality of portions of a dentition;
assign numeric values to the portions, the numeric values corresponding to the severity diagnoses, wherein the numeric values corresponding to the severity diagnoses differ based on the number of dentulous portions of the dentition;
obtain a raw score based on the numeric values; and
determine a disease score based on the raw score, the disease score corresponding to a periodontal disease state of the dentition, wherein the disease score describes both the severity and the extent of periodontal disease in the dentition; and
output the disease score to a user.

17. The machine-readable medium of claim 16, wherein determining the disease score comprises correlating the raw score to the disease score.

18. The machine-readable medium of claim 16, wherein the portions comprise sextants of the dentition.

19. The machine-readable medium of claim 16, wherein the severity diagnoses comprise one or more of healthy, gingivitis, mild periodontitis, moderate periodontitis, and severe periodontitis.

20. The machine-readable medium of claim 19, wherein the severity diagnoses are determined based on bleeding that occurs upon probing in the portion, tooth pocket depth in the portion, and radiographic bone distance from a cemento-enamel junction in the portion.

21. The machine-readable medium of claim 16, further comprising instructions to:
use the disease score to determine a premium for an insurance policy.

22. The machine-readable medium of claim 21, further comprising instructions to:
monitor a change in the disease score over time; and
adjust the premium in accordance with the change.

23. A computer-implemented method of describing a periodontal disease state, comprising:
receiving multiple inputs for each of a plurality of portions of a dentition, the multiple inputs comprising at least two factors associated with the patient's periodontal tissues, the at least two factors being selected from the group consisting of bleeding that occurs upon probing; tooth pocket depth, and radiographic bone distance from a cemento-enamel junction,
assigning a severity diagnoses to each of the portions of the dentition, the severity diagnoses corresponding to periodontal disease states and being based on the received inputs based on the observations of the periodontal tissues and a predetermined correlation between the inputs for the at least two observations of the periodontal tissues and a severity diagnosis;
assigning, using a computer system configured to calculate a raw score and determine a disease score using a look up table, numeric values to the portions of the dentition, the numeric values corresponding to the severity diagnoses for each of the portions of the dentition, wherein the numeric values corresponding to the severity diagnoses differ based on the number of dentulous portions of the dentition;
calculating, using the computer system configured to calculate the raw score and determine the disease score using a look up table, the raw score based on the numeric values assigned to the portions of the dentition by summing the numeric values for each of the portions of the dentition; and
using the look up table to determine the disease score based on the raw score, the disease score corresponding to a periodontal disease state of the dentition and being based on the periodontal disease states of multiple different portions of the dentition; providing the disease score to a user.

24. The method of claim 23, wherein the portions comprise sextants of the dentition and the disease score is based on the number of sextants of the dentition that include teeth.

25. The method of claim 23, wherein the computer system configured to calculate the raw score and determine the disease score using the look up table comprises the computer system programmed to calculate the raw score and determine the disease score.

26. A computer-implemented method of describing a periodontal disease state, comprising:
receiving a first input and a second input for each of a plurality of portions of a dentition, the first and second inputs being based on observations of periodontal tissues for each portion of the dentition;
assigning a severity diagnoses to each of the portions of the dentition, the severity diagnoses being based on the first and second inputs for the portion of the dentition where each combination of the first and second inputs is associated with a pre-determined severity diagnosis;
assigning, using a computer system configured to calculate a raw score and determine a disease score using a look up table, numeric values to the portions of the dentition, the numeric values corresponding to the severity diagnoses for each of the portions of the dentition;
calculating, using the computer system configured to calculate the raw score and determine the disease score using the look up table, the raw score based on the numeric values assigned to the portions of the dentition; and
using the look up table to determine the disease score based on the raw score, the disease score corresponding to a periodontal disease state of the dentition and being based on the periodontal disease states of multiple different portions of the dentition; and
providing the disease score to a user.

27. The method of claim 26, wherein the computer system configured to calculate the raw score and determine the disease score using the look up table comprises the computer system programmed to calculate the raw score and determine the disease score.

28. A computer-implemented method of describing a periodontal disease state, comprising:
- receiving multiple inputs for each of a plurality of portions of a dentition, the inputs being based on observations of periodontal tissues for each portion of the dentition;
- assigning a severity diagnoses to the portions of the dentition, the severity diagnoses corresponding to periodontal disease states and being based on the received inputs based on the observations of the periodontal tissues;
- assigning, using a computer system configured to calculate a raw score and determine a disease score using a look up table, numeric values to the portions of the dentition, the numeric values corresponding to the severity diagnoses;
- calculating, using the computer system configured to calculate the raw score and determine the disease score using a look up table, the raw score based on the numeric values assigned to the portions of the dentition;
- using the look up table to determine the disease score based on the raw score, the disease score corresponding to a periodontal disease state of the dentition and being based on the periodontal disease states of multiple different portions of the dentition; and
- monitoring a change in the disease score over time, wherein the disease score increases and decreases based on therapeutic response.

* * * * *

UNITED STATES PATENT AND TRADEMARK OFFICE
CERTIFICATE OF CORRECTION

| | | |
|---|---|---|
| PATENT NO. | : 8,267,689 B2 | Page 1 of 1 |
| APPLICATION NO. | : 11/281241 | |
| DATED | : September 18, 2012 | |
| INVENTOR(S) | : John A. Martin, Roy C. Page and Carl F. Loeb | |

It is certified that error appears in the above-identified patent and that said Letters Patent is hereby corrected as shown below:

On the Title Page:

Item (56), Col. 2 (Other Publications), Line 1, Delete "Retreived" and insert -- Retrieved --

Signed and Sealed this
Twentieth Day of November, 2012

David J. Kappos
*Director of the United States Patent and Trademark Office*